(12) United States Patent
Mittal et al.

(10) Patent No.: US 9,254,257 B2
(45) Date of Patent: Feb. 9, 2016

(54) METHOD FOR TREATMENT OF ACNE USING PHARMACEUTICAL COMPOSITIONS OF CLINDAMYCIN

(75) Inventors: Ravindra Mittal, Gujarat (IN);
Sunilendu Bhushan Roy, Gujarat (IN);
Jay Shantilal Kothari, Gujarat (IN);
Shafiq Sheikh, Gujarat (IN); Jitendra Dasharathlal Patel, Gujarat (IN);
Jinesh Suresh Pancholi, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 63 days.

(21) Appl. No.: 13/880,107

(22) PCT Filed: Oct. 18, 2011

(86) PCT No.: PCT/IN2011/000719
§ 371 (c)(1),
(2), (4) Date: Jul. 1, 2013

(87) PCT Pub. No.: WO2012/053010
PCT Pub. Date: Apr. 26, 2012

(65) Prior Publication Data
US 2013/0266654 A1    Oct. 10, 2013

(30) Foreign Application Priority Data

Oct. 21, 2010  (IN) .......................... 2935/MUM/2010
Jul. 28, 2011  (IN) .......................... 2155/MUM/2011

(51) Int. Cl.
*A61K 9/00*        (2006.01)
*A61K 9/107*       (2006.01)
*A61K 31/7056*     (2006.01)
*A61K 8/49*        (2006.01)
*A61Q 19/00*       (2006.01)

(52) U.S. Cl.
CPC .................. *A61K 9/0014* (2013.01); *A61K 8/49* (2013.01); *A61K 9/1075* (2013.01); *A61K 31/7056* (2013.01); *A61Q 19/00* (2013.01); *A61Q 19/005* (2013.01); *A61Q 19/007* (2013.01); *A61K 2800/412* (2013.01)

(58) Field of Classification Search
CPC .............. A61K 9/0014; A61K 9/1075; A61K 31/7056; A61K 2800/412; A61Q 19/005

USPC ............................................ 424/489; 514/24
See application file for complete search history.

(56) References Cited

U.S. PATENT DOCUMENTS 6,113,921 A  *  9/2000  Friedman et al. ............. 424/400

FOREIGN PATENT DOCUMENTS

WO      2010/096868 A1    9/2010

OTHER PUBLICATIONS

Cunliffe et al.; Title: A randomized, double-blind comparison of a clindamycin phosphate/benzoyl peroxide gel formulation and a matching clindamycin gel with respect to microbiologic activity and clinical efficacy in the topical treatment of acne vulgaris; Clinical Therapeutics, vol. 24, Issue 7, pp. 1117-1133, Published Jul. 2002.*
Sigma-Aldrich, Title: Tyloxapol nonionic surfactant, product information, downloaded from http://www.sigmaaldrich.com/catalog/product/sigma/t8761?lang=en&region=US on Apr. 13, 2015..*
Varaporn Buraphacheep Junyaprasert, et al: "Enhancement of the skin permeation of clindamycin phosphate by Aerosol OT/1-butanol microemulsions", Drug Development and Industrial Pharmacy, New York, NY, US, vol. 33, No. 8, Aug. 1, 2007, pp. 874-880, XP008152562, ISSN: 0363-9045, DOI: 10.1080/03639040600975097 DOI: http://dx.doi.org/10.1080/03639040600975097.
Date A A et al: "Novel drug delivery systems: Potential in improving topical delivery of autiache agents", Skin Pharmacology and Physiology: Journal of Pharmacological Andbiophysical Research, S. Karger AG, Basel, CH, vol. 19, No. 1, Dec. 1, 2005, pp. 2-16, XP008152560, ISSN: 1660-5527, DOI: 10.1159/000089138 DOI: http://dx.doi.org/10.1159/000089138.

* cited by examiner

*Primary Examiner* — Johann R Richter
*Assistant Examiner* — Yanzhi Zhang
(74) *Attorney, Agent, or Firm* — Ladas & Parry LLP

(57)  ABSTRACT

The present invention relates to a method for treating, reducing or preventing acne. In particular, the present invention relates to methods for reducing the total number, incidence and severity of acne lesions on the skin which includes both inflammatory and non-inflammatory lesions. Further, the invention relates to reducing the incidence and severity of adverse events resulting from topical application of anti-acne agents resulting in improvement of skin tone. The method includes administering a novel and stable topical anti-acne pharmaceutical composition.

16 Claims, 3 Drawing Sheets

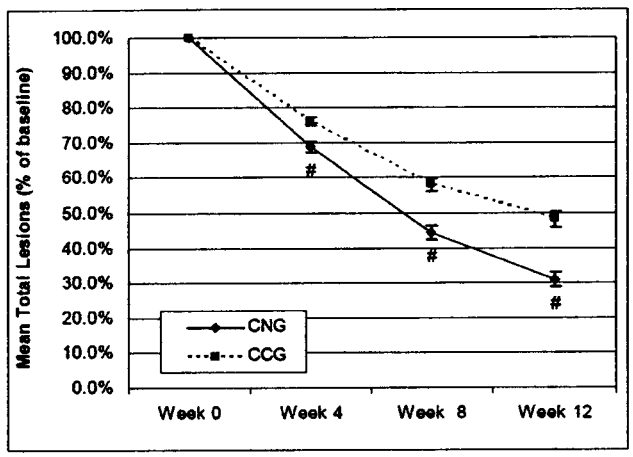

CNG = Clindamycin Nano-emulsion gel, CCG = Clindamycin conventional gel, I-bars = SE (Standard Error of Mean), CNG group: n=100, CCG group: n=100, #P<0.001

Figure 1: The mean % reduction in total lesions during the course of study as compared to baseline.

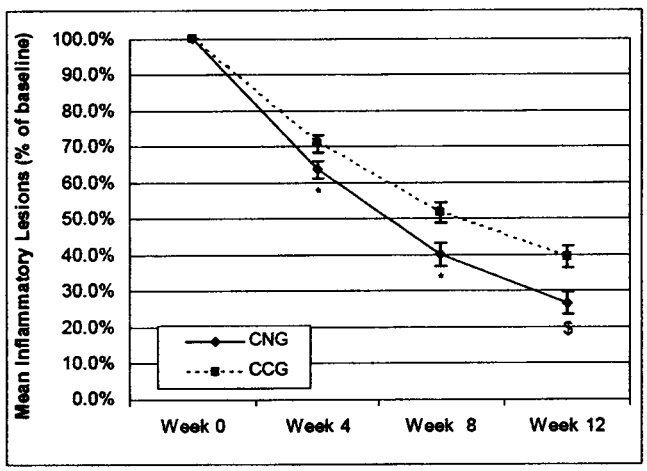

CNG = Clindamycin Nano-emulsion gel, CCG = Clindamycin conventional gel, I-bars = SE (Standard Error of Mean), CNG group: n=100, CCG group: n=100, *P<0.05, $P<0.005,

Figure 2: The mean % reduction in inflammatory lesions during the course of study as compared to baseline.

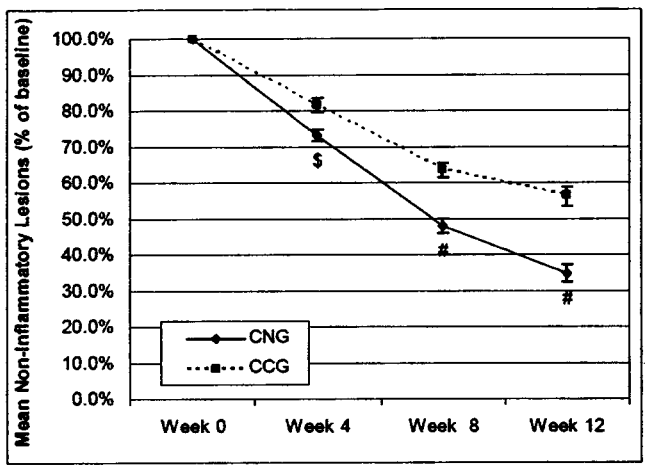

CNG = Clindamycin Nano-emulsion gel, CCG = Clindamycin conventional gel, I-bars = SE (Standard Error of Mean), CNG group: n=100, CCG group: n=100, $P<0.005, #P<0.001

Figure 3: The mean % reduction in non-inflammatory lesions during the course of study as compared to baseline.

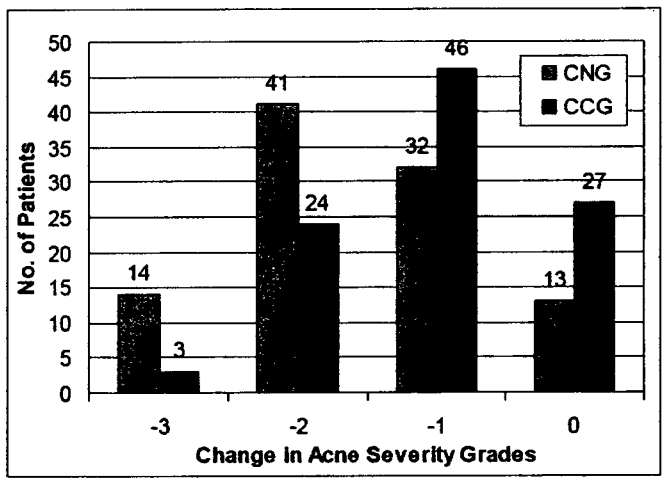

CNG = Clindamycin Nano-emulsion gel, CCG = Clindamycin conventional gel, CNG group: n=100, CCG group: n=100

Figure 4: The change in acne severity grades during the course of study in both the treatment groups (CNG Group and CCG Group).

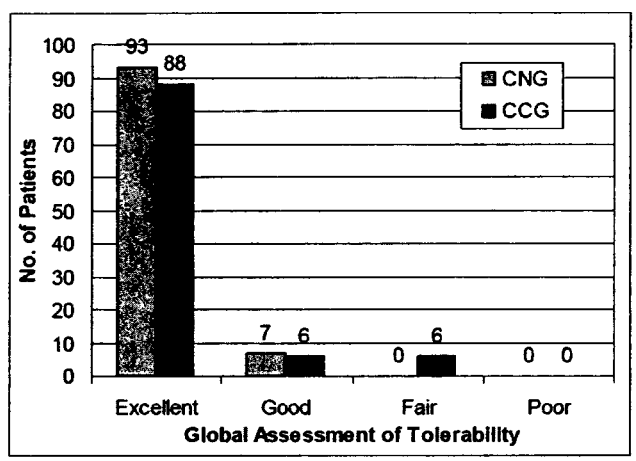
NG = Clindamycin Nano-emulsion gel, CCG = Clindamycin conventional gel, CNG group: n=100. CCG group: n=100
Figure 5: Overall assessment of tolerability at the end of the study.

METHOD FOR TREATMENT OF ACNE USING PHARMACEUTICAL COMPOSITIONS OF CLINDAMYCIN

RELATED APPLICATION INFORMATION

This application is a 371 of International Application PCT/IN2011/000719 filed 18 Oct. 2011 entitled "Method For Treatment Of Acne Using Pharmaceutical Compositions Of Clindamycin", which was published in the English language on 26 Apr. 2012, with International Publication Number WO 2012/053010 A2 and which claims priority from Indian Patents Applications 2935/MUM/2010, filed 21 Oct. 2010 and 2155/MUM/2011 filed 28 Jul. 2011, the content of which are incorporated herein by reference.

FIELD OF THE INVENTION

The present invention relates to a method for treating, reducing or preventing acne. In particular, the present invention relates to methods for reducing the total number, incidence and severity of acne lesions on the skin which includes both inflammatory and non-inflammatory lesions. Further, the invention relates to reducing the incidence and severity of adverse events resulting from topical application of anti-acne agents resulting in improvement of skin tone. The method includes administering a novel and stable topical anti-acne pharmaceutical composition.

BACKGROUND OF THE INVENTION

Acne vulgaris is a skin condition that affects over 85% of all people. Acne is a term for a medical condition of plugged pores typically occurring on the face, neck, and upper torso. Following are four primary factors that lead to the formation of acne vulgaris; (1) increased sebum output resulting in oily, greasy skin; (2) increased bacterial activity normally due to an overabundance of Propionibacterium acnes bacteria; (3) plugging (hypercornification) of the follicle or pilosebaceous duct; and (4) production of inflammation by substances leaking into the dermis which cause inflammatory reactions. The plugged pores result in blackheads, whiteheads, pimples or deeper lumps such as cysts or nodules. Severe cases of acne can result in permanent scarring or disfiguring.

Acne occurs when the oil glands of the skin called sebaceous glands produce an increased amount of oil. The sebaceous glands are connected to canals in the skin called hair follicles that terminate in openings in the skin called pores. The increased amount of oil secreted by the sebaceous glands is caused by an increase in androgen hormones in both males and females during adolescence or puberty. Accompanying the increase in the amount of oil secreted by the sebaceous glands is an increase in the shedding of the skin lining the hair follicles. The increase in the amount of secreted oil in combination with the increase in the shedding of the skin lining the hair follicles increases the likelihood of the pores being clogged by the shedding skin. A pore clogged by the shedding skin is referred to as a comedo.

The Propionibacterium acnes (P. acnes) normally reside on the skin. The propionibacterium acnes invade the clogged follicles and grow in the mixture of oil and cells in the hair follicle. It produces chemicals that stimulate inflammation resulting in acne. Acne lesions range in severity from blackheads, whiteheads and pimples to more serious lesions such as deeper lumps, cysts and nodules.

In many instances, the inflammation within the acne lesion provides an opportunity for secondary infections to invade and grow in the inflamed hair follicle. Some of these secondary infections can be more serious and more resistant to treatment than the primary Propionibacterium acnes infection.

Various products and methods are currently available for treatment of acne. The only products that have anti-sebum activity are estrogens and 13 cis-retinoic acid (isotretinoin) and these must be used systemically to be effective. Isotretinoin is used to treat only severe cystic or conglobate acne (Anja Thielitz et al., JDDG, 6, 2008, Pp: 1023-1031). Because of its teratogenic properties, birth defects can occur. Isotretinoin is a powerful drug and can elevate triglycerides, total cholesterol and decrease high-density lipoproteins (HDL). Other side effects include dry skin, dry eyes, itching, headaches, nosebleed, and photosensitivity. It is generally taken for 4-5 months to see improvement. However, all topical retinoic acid preparations may be irritating, and this may contribute to underutilization in clinical practices (Cynthia E Irby et al., J. of Adolescent Health, 43, 2008, Pp-421-424). Recently, one brand of oral contraceptive has been approved for the treatment of acne for patients who request birth control.

A number of topical and systemic agents are used to lower the number of bacteria that colonize the follicular duct. These include benzoyl peroxide (BP), and BP (5%), erythromycin (3%) combination (Benzamycin®). BP has antibacterial activity and drying effects and is available over the counter or by prescription. BP is applied once or twice daily for 1-2 months. BP can produce erythema and peeling of skin. BP is often tried first for both non-inflammatory and mild inflammatory acne. Other topical antibiotics include clindamycin and erythromycin. It is known that the combination of topical antibiotic such as clindamycin with other topical agents is more therapeutically effective than either drug used alone (James Q. Del Rosso et al., Drug therapy Topics, Volume 85; January 2010, Pp: 15-24). These topical antibiotics are used as solutions, lotions or gels by prescription only. Usually they are applied once or twice daily and results are seen in 1-2 months. Another topical agent, azelaic acid 20% (Azelex®) also has mild antibacterial effects.

Systemic antibiotics include tetracycline and its analogs, which are used in low doses for years or until the end of the acne prone years. Most patients with mild inflammatory acne receive a combination of topical antibiotics and tretinoin or other retinoid. Bacterial resistance does occur so antibiotics may be changed or BP is substituted since resistance does not occur with BP. More severe acne requires systemic antibiotics and topical retinoid. The most severe must receive oral isotretinoin for 4-5 months.

Various topical products containing clindamycin phosphate, adapalene or their combination are currently available in market. For example, Clindac® 1% clindamycin gel [marketed by Galderma], Adaferrin® 0.1% adapalene gel [marketed by Galderma], Deriva® MS 0.1% micropshere adapalene gel [marketed by Glenmark Pharmaceuticals Ltd.], Achilles®-C 0.1% adapalene and 1% clindamycin gel [marketed by Sandoz Ltd.].

There are no drugs that directly affect the inflammatory acne. The retinoids do have some anti-inflammatory properties, but these are poorly described. Topical steroid and even systemic steroids have been used to abort a severe flare of fulminant acne, but these are limited uses because of the side effects. Benzoyl peroxide gels are sometimes used as first aid on acne lesions. These function as a "drawing poultice", but data supporting this use is not available.

The treatment for acne centers around opening the pore, killing P. acnes, reducing sebum production and regulating inflammatory responses. Retinoids are the agents to reduce sebum production and open the pore. As a topical agent, adapalene (Differin®) or tretinoin (Retin-A®) is used for mild and moderate acne.

It is often advantageous to be able to deliver the drug over a period of time, such that a desired level of the drug in the target tissue is achieved for a period of time sufficient to achieve the desired result, e.g., killing most of a population of infectious bacterial. Dermatological conditions, such as acne, require multiple delivery strategies because they have multiple delivery requirements, such as killing skin surface bacteria while also penetrating deep into inflamed sebaceous glands to kill bacteria in that locus.

U.S. Patent Publication No. 2010/0015216 discloses composition for the treatment of acne comprising: a first therapeutic agent selected from the group consisting of salicylic acid, azelaic acid, adapalene, benzoyl peroxide, antibiotics and combinations thereof; and a second therapeutic agent which comprises a taurine species.

U.S. Pat. No. 5,962,571 discloses a pharmaceutical composition for the treatment of acne having an acne reduction component in an amount sufficient to reduce the redness and blemishes associated with acne.

U.S. Patent Publication No. 2010/0029781 discloses a method of preparing a solvent-microparticle (SMP) topical gel formulation comprising a bioactive drug wherein the formulation comprises the drug dissolved in a liquid and the drug in a microparticulate solid form dispersed in the liquid.

U.S. Patent Publication No. 2010/0068284 discloses a stable fixed dose topical formulation comprising therapeutically effective amounts of adapalene-containing microparticles and clindamycin. However, such formulation may not significantly reduce the incident and severity of acne lesions.

U.S. Pat. No. 5,894,019 discloses topical compositions comprising lipid and essentially free of emulsifiers and surfactants.

European Patent No. EP 0671903 B discloses topical compositions in the form of submicron oil spheres.

Most of the topical preparations contain vehicles comprising permeation enhancers, solvents, and high amount of surfactants to achieve topical compositions for acne treatment. But use of these agents is harmful, especially in chronic application, as many of them cause undesirable effects such as irritation and dryness and resulting in poor patient tolerability.

In general, current products are effective in reducing the clinical observation of acne but it does not completely eliminate the condition, hence the consumer is not completely satisfied with results of these products.

Although various over-the-counter products are commercially available to counteract acne condition, such as anti-acne agents for topical use, including salicylic acid, sulfur, lactic acid, glycolic acid, pyruvic acid, urea, resorcinol, N-acetylcysteine, retinoic acid, isotretinoin, tretinoin, adapalene, tazoretene, antibacterials such as clindamycin and erythromycin, vitamins such as zinc, folic acid and nicotinamide, benzoyl peroxide, octopirox, triclosan, azelaic acid, phenoxyethanol, phenoxypropanol, and flavinoids, however, these agents tend to lack in potential to mitigate the acne condition and may have negative side effects when devised in conventional topical formulations.

Therefore, despite of the wide availability of products for acne, there exists a need to improve effectiveness of anti-acne pharmaceutical agents by developing suitable topical preparations which facilitate drug permeation through the skin, and resulting in enhanced therapeutic activity alongside reducing the instance and severity of adverse events resulting from topical use of these agents.

SUMMARY OF THE INVENTION

In one general aspect there is provided a method for treating acne comprising administering a topical pharmaceutical composition comprising nano size droplets of clindamycin or salts thereof.

In another general aspect there is provided a method for reducing total number of acne lesions on the skin. The method comprises administering a topical pharmaceutical composition comprising nano size droplets of clindamycin or salts thereof.

In another general aspect there is provided a method for reducing total number of inflammatory acne lesions on the skin comprising administering a topical pharmaceutical composition comprising nano size droplets of clindamycin or salts thereof.

In another general aspect there is provided a method for reducing total number of non-inflammatory acne lesions on the skin comprising administering a topical pharmaceutical composition comprising nano size droplets of clindamycin or salts thereof.

In another general aspect there is provided a method for reducing the incidence and severity of acne lesions on the skin comprising administering a topical pharmaceutical composition comprising nano size droplets of clindamycin or salts thereof.

In another general aspect there is provided a method for reducing the incidence and severity of inflammatory acne lesions on the skin comprising administering a topical pharmaceutical composition comprising nano size droplets of clindamycin or salts thereof.

In another general aspect there is provided a method for reducing the incidence and severity of non-inflammatory acne lesions on the skin comprising administering a topical pharmaceutical composition comprising nano size droplets of clindamycin or salts thereof.

In another general aspect there is provided a method for reducing the incidence and severity of adverse events resulting from treatment of acne by the use of clindamycin, comprising administering a topical pharmaceutical composition comprising nano size droplets of clindamycin or salts thereof.

Embodiments of the method of treating acne may include one or more of the following features. Applying a topical pharmaceutical composition to the skin which composition further may includes one or more pharmaceutically acceptable excipients. For example, the pharmaceutically acceptable excipients may include one or more of lipids, oils, emulsifiers or surfactants, initiators, pH adjusting agents, emollients, humectants, preservatives, chelating agents, thickening agent, and the like.

In one general aspect there is provided a method for treating acne comprising administering a topical pharmaceutical composition prepared by the process comprising:

a) combining an oily phase comprising clindamycin or salts thereof along with other pharmaceutically acceptable excipients with an aqueous phase to form an emulsion;

b) reducing the particle size of emulsion of step a) to a droplet size having $D_{90}$ particle size of less than 500 nm; and c) mixing other pharmaceutically acceptable excipients to emulsion obtained in step b) and converting it into a suitable finished dosage form.

In another general aspect there is provided a method for improving the local and systemic tolerability of clindamycin comprising administering a stable topical pharmaceutical composition comprising nano size droplets of clindamycin or salts thereof.

The details of one or more embodiments of the invention are set forth in the description below. Other features, objects and advantages of the invention will be apparent from the description and claims.

BRIEF DESCRIPTION OF DRAWINGS

FIG. 1: The mean % reduction in total lesions during the course of study as compared to baseline.

FIG. 2: The mean % reduction in inflammatory lesions during the course of study as compared to baseline.

FIG. 3: The mean % reduction in non-inflammatory lesions during the course of study as compared to baseline.

FIG. 4: The change in acne severity grades during the course of study in both the treatment groups (CNG Group and CCG Group).

FIG. 5: Overall assessment of tolerability at the end of the study.

DETAILED DESCRIPTION OF THE INVENTION

The inventors of the invention have surprisingly found that when anti-acne agents or salts thereof are formulated into nano size droplets in pharmaceutically acceptable emulgel (emulsion gel) system which includes optimized ratios of oils and/or emulsifiers, the composition exhibits enhanced therapeutic efficacy and reduced incidence and severity of adverse events.

In particular, the inventors have found that the composition of the present invention significantly reduces the total number and severity of acne lesions, including inflammatory and non-inflammatory lesions. The composition was also found to reduce the incidence and severity of adverse events (such as local irritation, dryness, erythema, itching and photosensitivity) resulting from administration of anti-acne agents.

Further, advantageously the composition also posses stable thermodynamic properties and do not have the problems of creaming, flocculation, coalescence or sedimentation, which are commonly associated with macro-emulsion, thus ensuring better stability and longer shelf-life of the resulting product.

Moreover, the composition of the invention results in immediate and sustained action, covering large surface area with less quantity and posses good spreadability. The composition is also non-irritant to skin and mucous membranes, requires reduced frequency of application, thus leading to improved patient compliance and offers cosmetic benefits like non-stickiness, and non-greasy feel.

The term "acne" includes inflammatory diseases of the pilosebaceous follicles and/or skin glands, and commonly is characterized by papules, pustules, cysts, nodules, comedones, other blemishes or skin lesions. The term "acne" as used herein includes all known types of acne. Some types of acne which can be treated with the composition of the present invention are, for example, acne vulgaris, acne comedo, papular acne, premenstrual acne, preadolescent acne, acne venenata, acne cosmetica, pomade acne, acne detergicans, acne excoriee, gram negative acne, pseudofolliculitis barbae, folliculitis, perioral dermatitis, hiddradenitis suppurativa, cystic acne, acne atrophica, bromide acne, chlorine acne, acne conglobata, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea.

The terms "treating" or "treatment" of a state, disorder or condition as used herein means: (1) inhibiting the state, disorder or condition, i.e., arresting or reducing the development of the disease or at least one clinical or sub-clinical symptom thereof, or (2) relieving the disease, i.e., causing regression of the state, disorder or condition or at least one of its clinical or subclinical symptoms. The benefit to a subject to be treated is either statistically significant or at least perceptible to the patient or to the physician.

The embodiments of the present invention relates to various methods related to treatment of acne comprising applying to the afflicted skin region a pharmaceutical composition comprising one or more anti-acne agents or salts thereof in the form of nano size droplets, such as a non-gel emulsion.

In a preferred embodiment, the nano size droplets of anti-acne agents or salts thereof posses a $D_{90}$ particle size of less than about 500 nm.

In a further embodiment, the nano size droplets of anti-acne agents or salts thereof posses a $D_{90}$ particle size of about 250 nm, and more preferably about 100 nm.

In an embodiment, the method according to the present invention can be used to reduce the total number and the incidence & severity of acne lesions on the skin.

In a further embodiment, the method according to the present invention can be used to reduce the number and the incidence & severity of inflammatory acne lesions on the skin.

In a further embodiment, the method according to the present invention can be used to reduce number and the incidence & severity of non-inflammatory acne lesions on the skin.

In a further embodiment, the method according to the present invention can be used to reduce the incidence and severity of adverse events resulting from the topical application of anti-acne agents and thus increase compliance of the administration of anti-acne products.

In a further embodiment, the method according to the present invention can be used to improve the skin tone.

In a yet another embodiment, the method according to the present invention can be used to reduce sebaceous gland output.

Anti-acne agent for the purpose of the present invention may be selected from, but not limited to one or more of adapalene, azelaic acid, benzoyl peroxide, salicylic acid, sulfur, lactic acid, glycolic acid, pyruvic acid, urea, resorcinol, N-acetylcystein, retinoic acid, zinc, folic acid, nicotinamide, octopirox, triclosan, phenoxyethanol, phenoxypropanol, clindamycin, erythromycin, tretinoin, isotretinoin, sodium sulfacetamide, tazarotene, spirinolacton, or salts thereof.

In a preferred embodiment the composition comprises clindamycin or salts thereof.

In a further embodiment, the composition comprises about 0.5% to about 5.0% w/w, and preferably about 1.0% w/w of clindamycin or salt thereof (based on total weight of the composition).

The composition of the present invention further comprises one or more pharmaceutically acceptable excipients selected from, but not limited to lipids, oils, emulsifiers or surfactants, initiators, pH adjusting agents, emollients, humectants, preservatives, and chelating agents.

The pH of the composition of the invention ranges from about 4.5 to about 7.0, and preferably from 5.0 to about 6.5.

Suitable lipids which can be used include one or more of hydrocarbons, fatty alcohols, fatty acids, glycerides or esters of fatty acids with $C_1$-$C_{36}$ alkanols. Hydrocarbons may include paraffin or petroleum jelly. Fatty alcohols may include decanol, dodecanol, tetradecanol, hexadecanol or octadecanol. Fatty acids may include $C_6$-$C_{24}$ alkanoic acids such as hexanoic acid, octanoic acid, decanoic acid, dodecanoic acid, tetradecanoic acid, hexadecanoic acid, octadecanoic acid, unsaturated fatty acids such as oleic acid and linoleic acid. Glycerides may include olive oil, castor oil, sesame oil, caprylic/capric acid triglyceride or glycerol mono-, di- and tri-esters with palmitic and/or stearic acid. Esters of fatty acids may include $C_1$-$C_{36}$ alkanols such as beeswax, carnauba wax, cetyl palmitate, lanolin, isopropyl myristate, isopropyl stearate, oleic acid decyl ester, ethyl oleate and $C_6$-$C_{12}$ alkanoic acid esters and the like.

Suitable oils which can be used include one or more of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane, sunflower seed oil, tricaprylin (1,2,3 trioctanoyl glycerol), wheat germ oil and the like. The preferred quantity of oil used is in the range of about 5 to about 25% w/w, and more preferably in the range of about 5% to about 20% w/w of the composition.

Suitable emulsifiers or surfactant which can be used include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly(oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the emulsifiers/surfactant used is in the range of about 0.1% to about 10% w/w of the composition.

In a preferred embodiment, the ratio of emulsifier or surfactant to oil in the pharmaceutical composition of the present invention ranges from about 0.1:20 to about 0.1:1, preferably about 0.1:10 to about 0.1:1.

Suitable pH adjusting agents which can be used include one or more of organic or inorganic acids and bases including sodium hydroxide, potassium hydroxide, ammonium hydroxide, phosphate buffers, citric acid, acetic acid, fumaric acid, hydrochloric acid, malic acid, nitric acid, phosphoric acid, propionic acid, sulfuric acid, tartaric acid and the like.

Suitable emollients which can be used include one or more of caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, stearth-2 or -100, stearic acid, stearyl alcohol, urea and the like.

Suitable preservatives which can be used include one or more of phenoxyethanol, parabens (such as methylparaben and propylparaben), propylene glycols, sorbates, urea derivatives (such as diazolindinyl urea), and the like.

Suitable humectants which can be used include one or more of propylene glycol, glycerin, butylene glycol, sorbitol, triacetin and the like.

Suitable chelating agents which can be used include one or more of disodium EDTA, edetate trisodium, edetate tetrasodium, diethyleneamine pentaacetate and the like.

Suitable initiators may include one or more of alcohols like $C_1$-$C_{12}$ alcohols, diols and triols, glycerol, methanol, ethanol, propanol, octanol and the like.

In one embodiment, composition of the invention may be prepared by a) combining an oily phase comprising one or more anti-acne agents or salts thereof along with other pharmaceutically acceptable excipients with an aqueous phase to form an emulsion; b) reducing the particle size of emulsion of step a) to a droplet size having $D_{90}$ particle size of less than about 500 nm; and c) mixing other pharmaceutically acceptable excipients to emulsion obtained in step b) and converting it into a suitable finished dosage form.

The nano size droplets may be produced with reciprocating syringe instrumentation, continuous flow instrumentation, high speed mixing or high pressure homogenization. However, it will appreciated to the person skilled in the art any known method of reducing the size of droplet may be adopted to serve the purpose of the present invention.

Small droplets of the nano emulsion may be formed by passing the emulsion through a homogenizer under different pressures ranging from 3,500-21,500 psi. The emulsion may be passed between 4-5 times under the same conditions to get a final $D_{90}$ droplet size of less than about 500 nm. The nano droplets formed may be filtered through 0.2 to 0.4 micron filter.

The gel base may be used in the present invention to form a gel matrix for the preparation of nanogel from nano emulsion. The gel base comprises of one or more of thickening agents.

Suitable thickening agents which can be used include one or more of cellulose polymer, a carbomer polymer, a carbomer derivative, a cellulose derivative, polyvinyl alcohol, poloxamers, polysaccharides and the like.

Suitable dosage form of the invention may include cream, gel, ointment, lotion, paste, liniment, and emulsion.

In a preferred embodiment, the composition of the invention is in the form of gel.

The present invention further provides use of a pharmaceutical composition comprising clindamycin or salts thereof in the form of nano size droplets, for reducing the total number and severity of acne lesions on the skin; reducing the number and the incidence and severity of inflammatory acne lesions on the skin; reducing number and the incidence and severity of non-inflammatory acne lesions on the skin; reducing the incidence and severity of adverse events resulting from topical application of anti-acne agents; improving the skin tone of a mammal; or reducing sebaceous gland output.

The efficacy and safety of the composition of the present invention (containing 1% clindamycin phosphate) was evaluated vis-à-vis other marketed gel formulation (Clindac-A® Gel [marketed by Galderma International] containing 1% clindamycin phosphate). It was observed that the formulation of the present invention was more effective in reducing total number and the incidence and severity of lesions including inflammatory and non-inflammatory lesions and is better tolerated (both locally and systemically) than the marketed formulation. The composition of the present invention was also found to reduce the incidence and severity of adverse events resulting from its application when compared with the adverse events resulting from application of the marketed formulation.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1

Clindamycin Phosphate Nano Emulsion

TABLE 1

| Sr. No. | Ingredients | % w/w |
| --- | --- | --- |
| 1 | Clindamycin Phosphate | 1.00-4.00 |
| 2 | Polysorbate 80 | 4.00-8.00 |
| 3 | Glycerol | 7.00-13.00 |
| 4 | Soyabean oil | 14.00-20.00 |
| 5 | Disodium EDTA | 0.05-1.50 |
| 6 | Vitamin E Acetate | 0.05-0.50 |
| 7 | Water | Q.S. |

Procedure:

Clindamycin phosphate was dissolved in water, polysorbate 80, glycerol, vitamin E acetate and soyabean oil. The resulting blend was homogenized to reduce the droplet size to $D_{90}$ particle size of about 250 nm with the help of high pressure homogenization to get the nano emulsion.

Example 2

Clindamycin Phosphate Nanogel

TABLE 2

| Sr. No. | Ingredients | % w/w |
| --- | --- | --- |
| 1 | Clindamycin Phosphate | 0.50-3.00 |
| 2 | Alcohol | 3.00-7.00 |
| 3 | Polysorbate 80 | 1.00-5.00 |
| 4 | Glycerol | 3.00-7.00 |
| 5 | Soyabean oil | 7.00-11.00 |
| 6 | Disodium EDTA | 0.05-0.50 |
| 7 | Vitamin E Acetate | 0.05-0.50 |
| 8 | Carbopol 974P | 0.50-3.00 |
| 9 | Water | Q.S. |

Procedure:

Clindamycin phosphate was dissolved in water, alcohol, polysorbate 80, glycerol, soyabean oil, vitamin E acetate and disodium EDTA. The resulting blend was homogenized to reduce the droplet size to $D_{90}$ particle size of about 250 nm with the help of high pressure homogenization to get the nano emulsion. Sodium hydroxide solution was added to aqueous dispersion of Carbopol 974P to adjust the pH and finally it was mixed with nano emulsion to get nanogel.

Example 3

Clindamycin Phosphate Nano Emulsion

TABLE 3

| Sr. No. | Ingredients | Quantity % w/w |
| --- | --- | --- |
| 1 | Clindamycin Phosphate | 1.200 |
| 2 | Polysorbate 80 | 3.000 |
| 3 | Glycerol | 5.000 |
| 4 | Soybean oil | 9.000 |
| 5 | Disodium EDTA | 0.250 |
| 6 | Vitamin E Acetate | 0.100 |
| 7 | Carbopol 974P | 1.500 |
| 8 | Sodium Hydroxide | 0.332 |
| 7 | Water | Q.S. |

Procedure:

Clindamycin phosphate was dissolved in water, polysorbate 80, glycerol, soybean oil, vitamin E acetate and disodium EDTA. The resulting blend was homogenized to reduce the droplet size to $D_{90}$ particle size of about 250 nm with the help of high pressure homogenization to get the nano emulsion. Sodium hydroxide solution was added to aqueous dispersion of Carbopol 974P to adjust the pH and finally it was mixed with nano emulsion to get nanogel.

Example 4

Clinical Study

The efficacy and safety of the composition of the present invention (containing 1% clindamycin phosphate) was evaluated vis-à-vis other marketed gel formulation (Clindac-A® Gel [marketed by G alderma International), containing 1% clindamycin phosphate].

A total of 208 patients suffering from acne vulgaris of the face were enrolled in the clinical study; out of these 105 patients were randomized to the nano-emulsion gel (Composition of the invention or Nano-emulsion gel, CNG Group) arm; while 103 patients were randomized to the marketed gel product (Conventional gel, CCG Group) arm.

Patients were instructed to apply either of the medication to the acne affected areas twice daily (after bath in the morning and after washing & before retiring at night). A thin film of gel was to be applied, with the fingertips, avoiding the eyes and lips, ensuring that the affected areas were dry before application. The total duration of treatment was 12 weeks in each of the study treatment group. After the initiation of therapy, patients were followed-up on outpatient visits scheduled at weeks 4, 8 and 12 after the initiation of therapy.

The efficacy assessments were carried out by recording the number of non-inflammatory lesions (open & closed comedones), inflammatory lesions (papules, pustules, nodules and cysts) and total lesions. Acne severity was assessed by the following acne severity grades/scores (categorized in Table 4). Treatment success was defined as the attainment of "clear" or "almost clear" grades of acne severity score at the end of treatment phase.

TABLE 4

| Score | Grade | Description |
| --- | --- | --- |
| 0 | Clear | Normal appearing, clear skin with no evidence of acne vulgaris |
| 1 | Almost Clear | Rare non-inflammatory lesions present with rare non-inflmaed papules)papules must be resolving and may be hyperpigments, although not pink-red) |
| 2 | Mild | Non-inflammatory lesions predominate with multiple inflammatory lesions evident: several to many comedones and papules/pustules, and may or may not be one small nodulocystic lesion |

TABLE 4-continued

| Score | Grade | Description |
|---|---|---|
| 3 | Moderate | Non-inflammatory lesions predominate, with multiple inflammatory lesions evident: several to many comedones and papules/pustules, and there may not be one small nodulocystic lesion |
| 4 | Severe | Inflammatory lesions are more apparent, many comedones and papules/pustules, there may or may not be a few nodulocystic lesions |
| 5 | Very Severe | Highly inflammatory lesions predominate, variable number of comedones, many papules/pustules and many nodulocystic lesions |

Adverse events were recorded including date of onset and end (duration), intensity (mild, moderate or severe), treatment required and final outcome.

Statistical Analysis

Intention to treat (ITT) efficacy and safety assessments was carried out comprising of all the enrolled patients who had received treatment with the study medication and had undergone at least one post-baseline assessment. Last observation carried forward (LOCF) procedures were followed for missing data values. Primary efficacy variables were % improvement in total, inflammatory and non-inflammatory lesions at the end of therapy (i.e. week 12) and at each follow-up visit as compared to baseline (i.e. week 0). Secondary efficacy variables were treatment success rate and the degree of improvement in the acne severity score at the end of therapy (i.e. week 12) and at each follow-up visit as compared to baseline (i.e. week 0). Efficacy data are presented as mean, standard deviation (SD), standard error of mean (SE) and 95% confidence intervals (CI) for continuous variables (as specified) and frequency (number) and % of patients with each severity grade/score of acne. Statistical analysis was carried out using T-test, Chi-square Test, Fischer's Exact Test & Mann-Whitney U Test according to the data characteristics and distributions. P values <0.05 for two-tailed assessments were considered as statistically significant.

Efficacy Analysis

In all the enrolled patients in each of the treatment groups, acne lesions were reduced during the course of study after initiation of therapy. Significantly greater mean % reductions in total lesions (P<0.001), inflammatory lesions (P<0.005) and non-inflammatory lesions (P<0.001) were reported in CNG Group as compared to CCG Group at week 12 as shown in Table 5.

Pre-defined 'treatment success' was achieved in 53% [43.2-62.8%] of patients with CNG treatment while the same was achieved in 28.0% [19.8-36.2%] of patients with CCG treatment (P<0.001). The reduction in the mean acne severity score was 1.6±0.9 [1.49-1.73] in CNG group; while the same reduced by 1.0±0.8 [0.87-1.19] in CCG group at the end of study (P<0.001).

Further, mean % reductions in total, inflammatory and non-inflammatory lesions as compared to baseline (i.e. week 0) are shown in FIGS. 1, 2 & 3 respectively. The change in acne severity grades reported in the patients during the course of study in each of the treatment groups is shown in FIG. 4. Thus, 55% [45.2-64.8%] patients had at least two grade change (−3 or −2) in their acne severity at the end of treatment with CNG while 27% [18.9-35.1%] patients reported the same with CCG therapy (P<0.001).

TABLE 5

| Characteristics | CNG Group (n = 100) | CCG Group (n = 100) | P Value |
|---|---|---|---|
| Total Lesions | 73.4 ± 31.7% [67.2-79.6%] | 60.6 ± 31.3% [54.3-66.9%] | <0.005 |
| Inflammatory Lesions | 65.1 ± 23.8% [60.4-69.8%] | 43.7 ± 26.5% [38.6-48.9%] | <0.001 |
| Non-inflammatory Lesions | 69.3 ± 21.5% [65.0-73.5%] | 51.9 ± 22.2% [47.6-56.2%] | <0.001 |

Mean % reductions in acne lesions in both the study groups at week 12 as compared to baseline (Mean±SD [95% CI]) [CNG=Nano-emulsion gel, CCG=Conventional gel, SD=Standard Deviation, CI=Confidence Interval]

Safety Analysis

No 'serious' or 'severe' adverse event was reported in any of the patients enrolled in either of the study groups. None of the patients discontinued the study due to any adverse event in either of the study groups. 93.0% [88.0-98.0%] patients in CNG group and 88.0% [82.0-94.0%] patients in CCG group were rated to have an "excellent" tolerability with the therapy at the end of the study, according to the four-point global assessment of tolerability scale (P=0.228).

On tolerability assessment, the patient adverse event incidence rate reported in the study was 7% [2.0-12.0%] in CNG group and 12.0% [6.0-18.0%] in CCG group; which was not statistically significantly different between the study groups but was numerically in favour of the nano-emulsion gel formulation (P=0.346). Table 6 shows the list of adverse events reported in each of the treatment groups. Further, all the adverse events reported in CNG group were of "mild" intensity while; 5 (33.3% [9.5-57.2%]) of the 15 adverse events in CCG group were of "moderate" intensity (P=0.122). All these adverse events in both the treatment groups had "possible" association with the respective study medication and resolved with/without symptomatic treatment during the course of the study.

TABLE 6

| Sr. No. | Nature | CNG Group (n = 100) | CCG Group (n = 100) | P Value |
|---|---|---|---|---|
| 1 | Local Irritation | 2 (2.0%) | 6 (6.0%) | 0.279 |
| 2 | Itching | 1 (1.0%) | 5 (5.0%) | 0.212 |
| 3 | Dryness of skin | 2 (2.0%) | 3 (3.0%) | 1.000 |
| 4 | Erythema | 3 (3.0%) | 1 (1.0%) | 0.621 |
| | Total | 8 Events | 15 Events | 0.121 |

Significantly higher improvements in the mean percentages of inflammatory as well as total acne lesions were noticeable after CNG treatment as compared to CCG treatment, which were apparent as early as 4 weeks after treatment and persisted thereafter. Improvements in non-inflammatory lesions in CNG group were also significantly better at 4 weeks and thereafter. Treatment success rate at the end of study was almost twice with CNG treatment than with CCG. Similarly, the change in acne severity of at least 2 grades was reported in double the number of patients receiving CNG than CCG. It was also noticeable that an incremental treatment response was observed throughout the course of the study and a "plateau" effect was not noticeable till the end of 12 weeks of therapy.

Further, none of the patients discontinued the study due to any adverse event in either of the study groups. 93.0% [88.0-98.0%] patients in CNG group and 88.0% [82.0-94.0%] patients in CCG group were rated to have an "excellent"

tolerability with the therapy at the end of the study, according to the four-point global assessment of tolerability scale (P=0.228). FIG. 5 shows the complete global assessment of tolerability as given by the investigators.

The results of the present study suggest that clindamycin nano-emulsion gel formulation leads to a significantly better as well as earlier response on the inflammatory acne lesions and was well tolerated by patients. Improved penetration of clindamycin into the infected pilo-sebaceous units with the synergistic bactericidal effects of the nano-emulsion itself could be responsible for these observations.

Moreover, enhanced inhibitory effect of clindamycin on *P. acnes* along with its anti-inflammatory effects altering the incompletely understood natural history of comedone formation is a possible explanation for the improvement in noninflammatory lesions. Better moisturizing properties of the nano-emulsion gel and optimized anti-inflammatory properties of clindamycin in the pilo-sebaceous glands could have lead to favourable local tolerance observed.

The study thus demonstrates that the novel nano-emulsion gel formulation of the present invention is more effective in reducing both inflammatory as well as the non-inflammatory acne lesions than the marketed formulation. Adverse events of local irritation reported with the nano-gel formulation of the invention are also less frequent and milder in intensity than the comparator. Thus, the results indicate that the nano-gel formulation of the present invention produces better therapeutic response in the treatment of acne vulgaris of the face, has a better safety profile and well tolerated than the marketed formulation.

While the invention has been described in terms of its specific embodiments, certain modifications and equivalents will be apparent to those skilled in the art and are intended to be included within the scope of the invention.

We claim:

1. A method for treating acne by administering a topical pharmaceutical nanogel composition of clindamycin or a salt thereof, the nanogel composition consisting of a nanoemulsion and a gel base, the nanoemulsion consists of nano size droplets of clindamycin or a salt thereof, 5% to 25% w/w oils/lipids, 0.1% to 10% w/w of emulsifiers and one or more pharmaceutically acceptable excipients consisting of initiators, pH adjusting agents, thickening agents, emollients, humectants, preservatives, and chelating agents.

2. The method as claimed in claim 1, wherein the method reduces total number of acne lesions on the skin.

3. The method as claimed in claim 2, wherein the method reduces the total number and severity of acne lesions on the skin.

4. The method as claimed in claim 1, wherein the method reduces the incidence and severity of adverse events resulting from the treatment of acne.

5. The method as claimed in claim 4, wherein the adverse event comprises one or more of local irritation, dryness, erythema, itching and photosensitivity.

6. The method as claimed in claim 2, wherein the acne lesions are inflammatory lesions.

7. The method as claimed in claim 2, wherein the acne lesions are non-inflammatory lesions.

8. The method as claimed in claim 1, wherein the nano size droplets of clindamycin or a salt thereof has a $D_{90}$ particle size of 500 nm or less.

9. The method as claimed in claim 1, wherein the nano size droplets of clindamycin or a salt thereof has a $D_{90}$ particle size of 250 nm or less.

10. The method as claimed in claim 1, wherein the nano size droplets of clindamycin or salt thereof has a $D_{90}$ particle size of 100 nm or less.

11. The method as claimed in claim 1, wherein the composition comprises about 0.5% to about 5.0% w/w of clindamycin or a salt thereof.

12. The method as claimed in claim 1, wherein the emulsifiers and oil are present in the composition in a weight ratio of from about 0.1:20 to about 0.1:1.

13. The method as claimed in claim 1, wherein the oils are selected from the group consisting of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane sunflower seed oil, tricaprylin (1.2.3 trioctanoyl glycerol), and wheat germ oil.

14. The method as claimed in claim 1, wherein the lipids are selected from the group consisting of hydrocarbons, fatty alcohols, fatty acids, glycerides and esters of fatty acids with $C_1$-$C_{36}$ alkanols.

15. The method as claimed in claim 1, wherein the emulsifiers are selected from the group consisting of ionic polysorbate, Nonylphenol Polyethylene Glycol Ethers, (alkylphenolhydroxypolyoxyethylene), Poly(oxy-1,2-ethanediyl), alpha-(4-nonylphenol)omega-hydroxy-, branched, Nonylphenol Polyethylene Glycol Ether mixtures, phenoxypolyethoxyethanols and polymers thereof, and sodium dodecyl sulfate.

16. The method as claimed in claim 1, wherein the composition is prepared by a process comprising:
 a) combining an oily phase comprising clindamycin or a salt thereof along with oils/lipids and emulsifiers with an aqueous phase to form an emulsion;
 b) reducing the particle size of emulsion of step a) to a droplet size having $D_{90}$ particle size of 500 nm or less; and
 c) mixing the nanoemulsion obtained in step b) with the gel base to form a nanogel.

* * * * *